US011408026B2

United States Patent
Hamilton et al.

(10) Patent No.: US 11,408,026 B2
(45) Date of Patent: Aug. 9, 2022

(54) METHODS OF PREDICTING SUSCEPTIBILITY TO INFECTIOUS DISEASE AND RELATED METHODS OF TREATMENT

(71) Applicant: LifeVault Bio, Inc., Waltham, MA (US)

(72) Inventors: Jonathon B. Hamilton, Littleton, MA (US); Salvatore G. Viscomi, Boston, MA (US); Trevor J. Perry, Whitinsville, MA (US)

(73) Assignee: LifeVault Bio, Inc., Waltham, MA (US)

( * ) Notice: Subject to any disclaimer, the term of this patent is extended or adjusted under 35 U.S.C. 154(b) by 0 days.

(21) Appl. No.: 17/240,991

(22) Filed: Apr. 26, 2021

(65) Prior Publication Data

US 2021/0332422 A1    Oct. 28, 2021

Related U.S. Application Data

(60) Provisional application No. 63/015,104, filed on Apr. 24, 2020.

(51) Int. Cl.
*C12Q 1/6827*     (2018.01)
*A61K 39/215*    (2006.01)

(52) U.S. Cl.
CPC .......... *C12Q 1/6827* (2013.01); *A61K 39/215* (2013.01)

(58) Field of Classification Search
None
See application file for complete search history.

(56) References Cited

U.S. PATENT DOCUMENTS

2017/0321284 A1   11/2017   McCarroll et al.
2018/0030412 A1    2/2018   Walsh et al.

FOREIGN PATENT DOCUMENTS

| WO | WO 2016/085876 |  | 6/2016 |
| WO | WO 2016/086197 |  | 6/2016 |
| WO | WO 2017/156416 | A1 | 9/2017 |
| WO | WO 2018/191440 | A1 | 10/2018 |
| WO | WO 2019/079493 |  | 4/2019 |

OTHER PUBLICATIONS

Chen et al., Clinical and immunological features of severe and moderate coronavirus disease 2019. J Clin Invest. 2020;130(5):2620-2629.*
Clary Estes. What Is The Cytokine Storm And Why Is It So Deadly For Coronavirus Patients?. https://www.forbes.com/sites/claryestes/2020/04/16/what-is-the-cytokine-storm-and-why-is-it-so-deadly-for-covid-19-patients/?sh=3aa321e5460f. Dayed Apr. 16, 2020.*
Cook et al. Comorbid and inflammatory characteristics of genetic subtypes of clonal hematopoiesis. Blood Adv. Aug. 27, 2019; 3(16):2482-2486.*
Gibson, Christopher J., et al. "Donor-engrafted CHIP is common among stem cell transplant recipients with unexplained cytopenias." *Blood, The Journal of the American Society of Hematology* 130.1 (2017): 91-94.
Jaiswal, Siddhartha, et al. "Age-related clonal hematopoiesis associated with adverse outcomes." *New England Journal of Medicine* 371.26 (2014): 2488-2498.
Shivarov, Velizar, and Milena Ivanova. "Clonal haematopoiesis and COVID-19: A possible deadly liaison." *International Journal of Immunogenetics* 47.4 (2020): 329-331.
Bick, Alexander G., et al., "Genetic interleukin 6 signaling deficiency attenuates cardiovascular risk in clonal hematopoiesis." *Circulation* 141.2 (2020): 124-131.
Cook, Elina K., et al., "Clonal hematopoiesis and inflammation: Partners in leukemogenesis and comorbidity." *Experimental hematology* 83 (2020): 85-94.
Frick, et al., "Role of Donor Clonal Hematopoiesis in Allogeneic Hematopoietic Stem-Cell Transplantation." *Journal of Clinical Oncology* 37(5): 375-385 (2018).
Frasez Soerensen, et al., "Therapy-Related Myeloid Neoplasms Following Autologous Stem Cell Transplantation: The Prevalence of Chip Mutations at Time of Transplantation—a Single Center Experience." *Blood* (2018) 132 (Supp. 1): 1529.
Husby, et al., "Clinical Impact of Clonal Hematopoiesis after Autologous Stem Cell Transplantation for Lymphoma: A National Population-Based Cohort Study." *Blood* (2018); 132 (Supplement 1): 607.
Li, et al., "Methyltransferase Dnmt3a upregulates HDAC9 to deacetylate the kinase TBK1 for activation of antiviral innate immunity." *Nature Immunology* (2016), 17 (7): 806-815.
Duployez, et al. "Clinico-Biological Features and Clonal Hematopoiesis in Patients with Severe COVID-19." *Cancers* (2020), 12(7): 1992.
Bolton, et al., "Clonal hematopoiesis is associated with risk of severe Covid-19." *medRxiv* [Preprint]. Nov. 27, 2020: doi: 10.1101/2020.11.25.20233163.
International Search Report issued in International Application No. PCT/US2021/29249, dated Sep. 1, 2021.

* cited by examiner

*Primary Examiner* — Nianxiang Zou
(74) *Attorney, Agent, or Firm* — Morse, Barnes-Brown & Pendleton, P.C.; Stanley F. Chalvire, Esq.; Erin E. Bryan, Esq.

(57) ABSTRACT

Disclosed herein are methods for predicting susceptibility to an infection based on the observation of specific mutations in blood cells, as well as methods for treating or reducing susceptibility to an infection in a subject.

20 Claims, No Drawings

METHODS OF PREDICTING SUSCEPTIBILITY TO INFECTIOUS DISEASE AND RELATED METHODS OF TREATMENT

RELATED APPLICATIONS

This application claims the benefit of U.S. Provisional Application No. 63/015,104, filed on Apr. 24, 2020. The entire teachings of the above application are incorporated herein by reference.

BACKGROUND OF THE INVENTION

Coronavirus disease 2019 (COVID-19) became a pandemic in early 2020. One of the reasons for its rapid and widespread diffusion is the presence of a large number of asymptomatic or paucisymptomatic patients, who are not recognized as infected and therefore contribute to the spread of the virus. Data on the spread of the virus have led scientists to think that the actual number of infected people is much higher than the number of positive tests. For example, in Italy a ratio of 1 positive patient tested for every 10 infected people is considered reasonable, leading to more than 1 million infected people (corresponding to more than 1.7% of the Italian population) in total.

Identifying not only individuals at risk of infection, but also those at high risk of morbidity and mortality is one of the most important challenges in reducing the social impact of the disease. In addition, the results provided by cellular, genetic and/or biomarker analyses could guide the development and implementation of desperately needed strategies for the development of new antiviral agents and opportunities for cell therapy.

SUMMARY OF THE INVENTION

The present inventions generally concern methods of identifying subjects at risk of developing a severe COVID-19 infection and/or severe complications from COVID-19 infection. For example, in certain embodiments, disclosed herein are methods of identifying a subject at risk of developing a severe complication from Coronavirus disease 2019 (COVID-19) infection, such methods generally comprising a step of determining whether the subject has clonal hematopoiesis of indeterminate potential (CHIP). In certain aspects, the step of determining whether the subject has CHIP comprises sequencing at least part of the genome of one or more cells in a blood sample of the subject to identify a mutation in one or more genes selected from the group consisting of DNMT3A, TET2, ASXL1, PPM1D, JAK2, TP53, SRSF2, KRAS and SF3B1, wherein the presence of said mutation indicates that the subject has CHIP and is at risk of developing a severe COVID-19 infection and/or a severe complication from COVID-19 infection.

In certain embodiments, the methods disclosed herein further comprise a step of treating a subject identified as having CHIP, or that is otherwise at risk of developing a severe COVID-19 infection or a severe complication from COVID-19 infection. For example, in certain aspects of the methods disclosed herein treating the subject comprises administering to the subject one or more agents or vaccines to reduce the subject's likelihood of contracting COVID-19 infection.

Also described herein are methods of treating a subject at risk of developing a severe Coronavirus disease 2019 (COVID-19) infection and/or severe complications from COVID-19 infection. For example, in certain embodiments, disclosed herein are methods of treating a subject at risk of developing a severe COVID-19 infection, such methods generally comprising a step of determining whether the subject has clonal hematopoiesis of indeterminate potential (CHIP). In certain aspects the step of determining whether the subject has CHIP comprises sequencing at least part of the genome of one or more cells in a blood sample of the subject to identify a mutation in one or more genes selected from the group consisting of DNMT3A, TET2, ASXL1, PPM1D, JAK2, TP53, SRSF2, KRAS and SF3B1; wherein the presence of said mutation indicates that the subject has CHIP and is at risk of developing a severe COVID-19 infection; and treating the subject having CHIP to reduce the subject's risk of contracting a severe COVID-19 infection. For example, in certain aspects of the methods disclosed herein treating the subject comprises administering to the subject one or more agents or vaccines to reduce the subject's likelihood of contracting COVID-19 infection.

In certain embodiments of the inventions disclosed herein, the subject is at risk of requiring hospitalization. In certain embodiments, the subject is under the age of about 30, 40, 50, 60, 70, 80, 90, 100 years old or older. In certain embodiments, the subject has a severe autoimmune disease. In yet other embodiments, the subject has a comorbid condition (e.g., a comorbid condition selected from the group consisting of cancer, cerebrovascular disease, chronic kidney disease, chronic obstructive pulmonary disease (COPD), diabetes mellitus, heart conditions, obesity, pregnancy, history of smoking, Down syndrome, human immunodeficiency virus (HIV), neurologic conditions, interstitial lung disease, pulmonary fibrosis, pulmonary hypertension, Sickle cell disease, solid organ or blood stem cell transplantation, substance use disorders, use of corticosteroids or other immunosuppressive medications, cystic fibrosis, thalassemia, asthma, hypertension, immune deficiencies, and liver disease). In certain embodiments, the comorbid condition is selected from the group consisting of cancer, cerebrovascular disease, chronic kidney disease, chronic obstructive pulmonary disease (COPD), diabetes mellitus, heart conditions, obesity, pregnancy, and history of smoking.

In certain aspects, the mutation is a somatic mutation. For example, in certain embodiments of the methods disclosed herein, the mutation is a somatic mutation in DNMT3A and/or TET2.

Also described herein are methods of treating an infection in a subject. The methods may comprise sequencing at least part of the genome of one or more cells in a blood sample of a subject in need of treatment; identifying in the blood sample a mutation in one or more genes selected from the group consisting of DNMT3A, TET2, ASXL1, PPM1D, JAK2, TP53, SRSF2, KRAS and SF3B1, wherein the presence of said mutation indicates an increased susceptibility to an infection; and treating the subject, for example, by vaccinating the subject and/or reducing the incidence of hematopoietic clones comprising the mutation in the subject's blood.

Also described herein are methods of treating an infection in a subject. The methods may comprise sequencing one or more nucleic acids selected from the group consisting of DNMT3A, TET2, ASXL1, PPM1D, JAK2, TP53, SRSF2, KRAS, and SF3B1 from one or more cells in a blood sample of the subject; detecting the presence of a mutation in the sequenced nucleic acids; and treating the subject by reducing the incidence of hematopoietic clones comprising the mutation (e.g., a mis-sense mutation) in the subject's blood.

The infection may be a viral or a non-viral infection. In some embodiments, the infection is a viral infection and the virus is a coronavirus (e.g., severe acute respiratory syndrome coronavirus (SARS-CoV), Middle East respiratory syndrome coronavirus (MERS-CoV), severe acute respiratory syndrome coronavirus 2 (SARS-CoV-2)), influenza (e.g., influenza A (e.g., H1N1, H5N1, H1N2, H2N1, H3N1, H3N2, H2N3) or influenza B), or respiratory syncytial virus (RSV). In some embodiments, the infection is a non-viral infection (e.g., a bacterial, fungal, yeast, parasitic, or prion infection). In certain embodiments, the infection is Coronavirus disease 2019 (COVID-19). In some embodiments, the infection results in respiratory distress and/or a cytokine storm.

Described herein are methods of treating a coronavirus (e.g., severe acute respiratory syndrome coronavirus (SARS-CoV), Middle East respiratory syndrome coronavirus (MERS-CoV), severe acute respiratory syndrome coronavirus 2 (SARS-CoV-2)) infection in a subject. The methods may comprise sequencing at least part of the genome of one or more cells in a blood sample of a subject in need of treatment; identifying in the blood sample a mutation in one or more genes selected from the group consisting of DNMT3A, TET2, ASXL1, PPM1D, JAK2, TP53, SRSF2, KRAS, and SF3B1, wherein the presence of said mutation indicates an increased susceptibility to an infection. In certain aspects, the method further comprises a step of treating the subject, for example, by vaccinating the subject or reducing the incidence of hematopoietic clones comprising the mutation in the subject's blood. Alternatively, in certain embodiments, the method further comprises a step of treating the subject by implementing measures intended to reduce the subject's exposure to the infection and/or likelihood of contracting such infection (e.g., self-isolation, quarantine and/or social distancing). In certain aspects, the treatment comprises administering one or more agents or vaccines to the subject to reduce the likelihood of contracting the infection and/or developing complications therefrom.

Also described herein are methods of predicting a subject's susceptibility to a coronavirus infection. The methods may comprise sequencing one or more nucleic acids selected from the group consisting of DNMT3A, TET2, ASXL1, PPM1D, JAK2, TP53, SRSF2, KRAS and SF3B1 from one or more cells in a blood sample of the subject; and detecting the presence of a mutation in the sequenced nucleic acids, and wherein the presence of the mutation indicates an increased susceptibility to a coronavirus infection.

In some embodiments, the gene or nucleic acid is selected from the group consisting of TET2, DNMT3A, PPM1D, JAK2, and combinations thereof. In some embodiments, the mutation is a mis-sense mutation, frame-shift mutation, nonsense mutation, or splice-site disruption. In some embodiments, the mutation is in DNMT3A in exons 7 to 23. In some embodiments, the mutation is a mis-sense mutation in DNMT3A selected from the group consisting of G543C, S714C, F732C, Y735C, R736C, R749C, F751C, W753C, and L889C. In some embodiments, the mutation is a V617F mutation in JAK2. In some embodiments, the mutation is a disruptive mutation in TET2. In some embodiments, the mutation is a disruptive mutation in PPM1D.

In some embodiments, the mutation increases inflammation, induces a pro-inflammatory state in the subject, or causes elevations in inflammatory cytokines. In some embodiments, the cytokines are or comprise interleukins (e.g., IL-6, IL-8, IL-1α, IL-1β, IL-12, IL-18), interferons (e.g., IFN-α, IFN-β, IFN-γ, IFN-λ), and/or tumor necrosis factors (IFN-α, IFN-β, IFN-γ, IFN-λ). In some embodiments, reducing the incidence of hematopoietic clones comprising the mutation in the subject's blood reduces inflammation or inflammatory cytokines in the subject.

In some embodiments, the methods described herein further comprise identifying in the blood sample at least one genetic variant selected from the group consisting of: ACE2, CRP, IL1A, IL1B, IL6, IL6R, CXCL8, IL10, IL12A, IL12B, IL18, IFITM3, TNF, LTA, LTB, IFN-α1, IFN-α2, IFN-α4, IFN-α5, IFN-α6, IFN-α7, IFN-α8, IFN-α10, IFN-α13, IFN-α14, IFN-α16, IFN-α17, IFN-α21, IFN-beta, IFN-epsilon, IFN-gamma, IFN-kappa, IFN-lambda, and IFN-omega.

In some embodiments, the subject is a human subject, and in some embodiments, is at least 20, 30, 40, 50, 60, 70 years of age or older. In some embodiments, the subject has a comorbid condition (e.g., cardiovascular disease, diabetes, asthma, emphysema, obesity, cancer).

In some embodiments, the one or more cells in the blood sample are nucleated cells. In some embodiments, the one or more cells in the blood sample are somatic cells.

Also described herein are methods of predicting a subject's susceptibility to a coronavirus infection. The methods may comprise sequencing DNMT3A nucleic acids from one or more cells in a blood sample of a subject; detecting the presence of a mis-sense mutation in the sequenced DNMT3A nucleic acids; sequencing TET2 nucleic acids from one or more cells in the blood sample of the subject; and detecting the presence of a disruptive mutation in the sequenced TET2 nucleic acids, wherein the presence of a mis-sense mutation in the sequenced DNMT3A nucleic acids and/or the TET2 nucleic acids indicates the subject's increased susceptibility to a coronavirus infection.

Also described herein are methods of treating an infection in a subject. The methods comprise sequencing at least part of the genome of one or more cells in a blood sample of a subject in need of treatment; identifying in the blood sample a somatic sequence mutation in one or more genes selected from the group consisting of DNMT3A, TET2, ASXL1, PPM1D, JAK2, TP53, SRSF2, KRAS and SF3B1; identifying in the blood sample a somatic structural chromosomal mutation in one or more genes selected from the group consisting of DNMT3A, TET2, ASXL1, PPM1D, JAK2, TP53, SRSF2, KRAS and SF3B1; and/or identifying in the blood sample a germline sequence mutation in one or more genes selected from the group consisting of DNMT3A, TET2, ASXL1, PPM1D, JAK2, TP53, SRSF2, KRAS and SF3B1, wherein the presence of one or more somatic sequence mutations, somatic structural mutations or germline sequence mutations indicates an increased susceptibility to an infection, and treating the subject by reducing the incidence of hematopoietic clones comprising the mutation in the subject's blood.

The above discussed, and many other features and attendant advantages of the present inventions will become better understood by reference to the following detailed description of the invention.

DETAILED DESCRIPTION OF THE INVENTION

For reasons that are not entirely clear, some individuals have dysfunctional immune systems that fail to keep a response to Coronavirus disease 2019 (COVID-19) in check, leading to an uncontrolled immune response. It is generally known that the virus triggers an overproduction of immune cells and their signaling molecules leading to a cytokine storm often associated with a flood of immune cells into the lungs and ultimately resulting in acute respiratory distress syndrome (ARDS).

Host immune responses to viral infections are generally known to comprise multiple intricate processes that coordinate together to play significant roles in the protection of the host. The understanding of the COVID 19 host interaction will require a comprehensive examination of various cellular, genetic and biomarker factors in a blood sample to elucidate the dynamics of host immune system response, many of which are unclear at this time. Bridging these gaps will pave the way for identifying not only individuals at risk of being infected but those at high risk for morbidity and mortality. In addition, the powerful data provided by cellular/genetic/biomarker analyses could guide strategies for development of novel antiviral agents and opportunities for cell therapy.

Described herein are methods for detecting and/or treating genetic variations associated with a dysfunctional immune response that results in an increased mortality risk in a subject. Also described herein are methods for identifying and/or treating subjects at risk of, e.g., susceptible to, a dysfunctional immune response associated with genetic variations. In some embodiments, a blood sample from the subject is sequenced and one or more genetic variations or mutations are identified. In some embodiments, genetic variations are identified in one or more genes selected from the group consisting of DNMT3A, TET2, ASXL1, PPM1D, JAK2, TP53, SRSF2, KRAS and SF3B1. A dysfunctional immune response may include an inflammatory and/or interferon response. In some embodiments, the one or more genetic variations result in increased mortality risk in a subject having an infection (e.g., COVID-19 infection).

Described herein are methods for treating infections in a subject comprising sequencing at least part of the genome of one or more cells in a blood sample of a subject in need of treatment; identifying in the blood sample a mutation in one or more genes selected from the group consisting of DNMT3A, TET2, ASXL1, PPM1D, JAK2, TP53, SRSF2, KRAS and SF3B1, wherein the presence of said mutation indicates an increased susceptibility to an infection; and treating the subject by reducing the incidence of hematopoietic clones comprising the mutation in the subject's blood. In some aspects, an identified mutation in the one or more genes selected from the group consisting of DNMT3A, TET2, ASXL1, PPM1D, JAK2, TP53, SRSF2, KRAS and SF3B1 is an indicator of clonal hematopoiesis of indeterminate potential (CHIP).

In some aspects, mutations are somatic sequence mutations, somatic structural chromosomal mutations, and/or germline sequence mutations. In some embodiments, somatic sequence mutations in one or more genes are identified in a blood sample. In some embodiments, somatic structural chromosomal mutations are identified in a blood sample. In some embodiments, germline sequence mutations are identified in a blood sample.

Sequencing of DNA can be performed on tissues or cells. Sequencing of specific cell types (for example, hematopoietic cells obtained by flow sorting) can identify mutations in specific cell types that provide specific predictive value. Some cell types may provide a greater predictive value than other cell types. In some embodiments, the one or more cells in a blood sample are nuclear cells, e.g., are somatic cells.

Sequencing can also be conducted in single cells, using appropriate single-cell sequencing strategies. Single-cell analyses can be used to identify high-risk combinations of mutations co-occurring in the same cells. Co-occurrence signifies that the mutations are occurring in the same cell clone and carry a greater risk, and therefore have a greater predictive value, than occurrence of the same mutations in different individual cells.

In some embodiments, at least part of the genome of one or more cells in a blood sample, e.g., of a subject in need of treatment, is sequenced. In some embodiments the part of the genome that is sequenced is limited to specific genes, the whole exome, or parts of an exome. For example, the sequencing may be whole exome sequencing (WES). Sequencing can be carried out according to any suitable technique, many of which are generally known in the art. Many proprietary sequencing systems are available commercially and can be used in the context of the present invention, such as for example from Illumina, USA. Single-cell sequencing methods are known in the art, as noted for example by Eberwine et al., Nature Methods 11, 25-27 (2014) doi:10.1038/nmeth.2769 Published online 30 Dec. 2013; and especially single cell sequencing in microfluidic droplets (Nature 510, 363-369 (2014) doi:10.1038/nature13437), the entire contents of which are incorporated herein by reference.

Sequencing may be performed of specific genes only, specific parts of the genome, or the whole genome. In some aspects, specific parts of a gene can be sequenced; for example, in DNMT3A, exons 7 to 23 can be sequenced. Where a part of a genome is sequenced, that part can be the exome. The exome is the part of the genome formed by exons, and thus an exon sequencing method sequences the expressed sequences in the genome. There are 180,000 exons in the human genome, which constitute about 1% of the genome, or approximately 30 million base pairs. Exome sequencing requires enrichment of sequencing targets for exome sequences; several techniques can be used, including PCR, molecular inversion probes, hybrid capture of targets, and solution capture of targets. Sequencing of targets can be conducted by any suitable technique.

Methods of identifying somatic structural chromosomal mutations and germline sequence mutations in blood samples are known to those of skill in the art. Examples of such methods are described in WO 2019/079493 and US 2017/0321284, both of which are incorporated herein by reference.

In some embodiments, a mutation (e.g., a mutation in one or more genes selected from the group consisting of DNMT3A, TET2, ASXL1, PPM1D, JAK2, TP53, SRSF2, KRAS and SF3B1) is identified in a blood sample (e.g., a blood sample from a subject). In certain aspects, the presence of a mutation indicates an increased susceptibility to an infection (e.g., a human subject's increased susceptibility to COVID-19 infection and/or the corresponding sequalae). In some aspects, the presence of a mutation indicates an increased susceptibility to an adverse clinical outcome due to a dysfunctional immune response (e.g., a human subject's increased susceptibility to developing respiratory distress, ARDS and/or cytokine storm). In some embodiments, a mutation in one or more genes is selected from the group consisting of DNMT3A, TET2, PPM1D, and JAK2. In certain embodiments, a mutation in DNMT3A is identified, e.g., in a blood sample. In certain embodiments, a mutation in TET2 is identified, e.g., in a blood sample. In certain embodiments, a mutation in PPM1D is identified, e.g., in a blood sample. In certain embodiments, a mutation in JAK2 is identified, e.g., in a blood sample.

DNMT3A is DNA (cytosine-5-1-methyltransferase 3 alpha and is encoded on chromosome 2 (HGMC 2978). ASXL1 is additional sex combs like transcriptional regulator 1 and is encoded on chromosome 20 (HGNC 18318). TET2 is tet methylcytosine dioxygenase 2 and is encoded on chromosome 4 (HGNC 25941). PPM1D is protein phosphatase, Mg2+/Mn2+ dependent, 1D and is encoded on chromosome 17 (HGNC 9277). JAK2 is janus kinase 2 and is encoded on chromosome 9 (HGNC 6192). TP53 is tumor protein p53 and is encoded on chromosome 17 (HGNC 11998). SRSF2 is serine and arginine rich splicing factor 2 and is encoded on chromosome 17 (HGNC 10783). KRAS is KRAS proto-oncogene and is encoded on chromosome 12 (HGNC 6407). SF3B1 is splicing factor 3b subunit 1 and is encoded on chromosome 2 (HGNC 10768).

Mutations in genes can be disruptive (e.g., they have an observed or predicted effect on protein function) or non-disruptive. A non-disruptive mutation is typically a mis-sense mutation, in which a codon is altered such that it codes for a different amino acid, but the encoded protein is still expressed. In some embodiments, somatic mutations may be mis-sense mutations or disruptive mutations (e.g., frame-shift, nonsense, or splice-site disruptions).

Putative somatic mutations include but are not limited to those alleles that comprise at least one of non-silent/disruptive nucleotide changes, indels, mis-sense mutations, frame-shifts, stop mutations (addition or deletion), read-through mutations, splice mutations; and a confirmed change not due to a sequencing error or artifact of the testing system.

In some embodiments, mutations in DNMT3A are predominantly mis-sense mutations. In some aspects, mutations (e.g., mis-sense mutations) in DNMT3A are localized in exons 7 to 23. In some aspects, mutations in DNMT3A are enriched for cysteine-forming mutations. A common base-pair change in somatic variants is a cytosine-to-thymine transition. In some embodiments, a mutation in DNMT3A is a mis-sense mutation selected from the group consisting of G543C, S714C, F732C, Y735C, R736C, R749C, F751C, W753C, and L889C. In some embodiments, mutations in TET2 and/or PPM1D are disruptive mutations. In some embodiments, a mutation in JAK2 is a V617F mutation. Additional non-limiting examples of mutations found in DNMT3A, TET2, ASXL1, PPM1D, JAK2, TP53, SRSF2, KRAS and SF3B1 are described in: Genovese, et al., "Clonal Hematopoiesis and Blood-Cancer Risk Inferred from Blood DNA Sequence" N Engl J Med (2014) 371: 2477-2487; Jaisawal et al., "Age-Related Clonal Hematopoiesis Associated with Adverse Outcomes" N Engl J Med (2014) 371:2488-2498; Bick, et al. "Genetic Interleukin 6 Signaling Deficiency Attenuates Cardiovascular Risk in Clonal Hematopoiesis" Circulation (2020) 141:124-131; Cook et al., "Clonal hematopoiesis and inflammation: Partners in leukemogenesis and comorbidity" Exp Hematol (2020) 83:85-94; Perner et al., "Roles of JAK2 in Aging, Inflammation, Hematopoiesis and Malignant Transformation" Cells (2019) 8(8) 854; Cook et al., "Comorbid and inflammatory characteristics of genetic subtypes of clonal hematopoiesis" Blood Adv. (2019) 3(16): 2482-2486; Uyanik et al., "DNA damage-induced phosphatase Wip1 in regulation of hematopoiesis, immune system and inflammation" Cell Death Discov (2017) 3, 17018; US 2017/0321284; and WO 2019/079493, all incorporated herein by reference.

In some embodiments, a blood sample obtained from a subject may further be sequenced to identify at least one additional genetic variant. For example, a blood sample may be sequenced to identify at least one genetic variant for a tumor necrosis factor (e.g., TNF, LTA, and LTB), interferon (e.g., IFN-α1, IFN-α2, IFN-α4, IFN-α5, IFN-α6, IFN-α7, IFN-α8, IFN-α10, IFN-α13, IFN-α14, IFN-α16, IFN-α17, IFN-α21, IFN-beta, IFN-epsilon, IFN-gamma, IFN-kappa, IFN-lambda, and IFN-omega), or interleukin (e.g., IL1A, IL1B, IL6, IL6R, CXCL8, IL10, IL12A, IL12B, and IL18). In some embodiments, at least one genetic variant is selected from the group consisting of ACE2, CRP, IL1A, IL1B, IL6, IL6R, CXCL8, IL10, IL12A, IL12B, IL18, IFITM3, TNF, LTA, LTB, IFN-α1, IFN-α2, IFN-α4, IFN-α5, IFN-α6, IFN-α7, IFN-α8, IFN-α10, IFN-α13, IFN-α14, IFN-α16, IFN-α17, IFN-α21, IFN-beta, IFN-epsilon, IFN-gamma, IFN-kappa, IFN-lambda, and IFN-omega.

A mutation in one or more genes may cause an increase in inflammation, induce a pro-inflammatory state in a subject, or cause an elevation in inflammatory cytokines (e.g., interleukins, interferons, and/or tumor necrosis factors). Examples of inflammatory cytokines include IL-6, IL-8, IL-1α, IL-1β, IL-12, IL-18, IFN-α, IFN-β, IFN-γ, IFN-λ, TNF-α, TNF-β, and TNF-γ.

In some embodiments, a subject has or is susceptible to an infection. An infection may be a viral infection or a non-viral infection. For example, a viral infection may be caused by a coronavirus, influenza, respiratory syncytial virus (RSV), among others. In some embodiments, a coronavirus is selected from the group consisting of severe acute respiratory syndrome coronavirus (SARS-CoV), Middle East respiratory syndrome coronavirus (MERS-CoV), and severe acute respiratory syndrome coronavirus 2 (SARS-CoV-2). In certain embodiments, an infection is Coronavirus disease 2019 (COVID-19). In some embodiments, influenza is influenza A or influenza B. Strains of influenza A include H1N1, H5N1, H1N2, H2N1, H3N1, H3N2, and H2N3. In some embodiments, a non-viral infection is a bacterial, yeast (e.g., fungal), parasitic, or prion infection. In some aspects, the viral or non-viral infection results in respiratory distress or complications (e.g., acute respiratory distress syndrome, interstitial pneumonia, other respiratory disease) and/or a cytokine storm. Additional symptoms or complications of the infection include lung damage, blood complications (e.g., blood clots, hemostatic derangement), central nervous system complications (e.g., encephalitis), kidney damage, organ failure, acute cardiac injury (e.g., cardiac arrest, coronary artery occlusion, heart failure, myocarditis, cardiomyopathy), and loss of smell or taste.

In some embodiments, a subject may be treated by reducing the incidence of hematopoietic clones comprising a mutation in one or more genes in the subject's blood. "Treat, "treatment," "treated," "treating," etc. refer to providing medical or surgical attention, care, or management to an individual. The individual is usually ill or injured, or at increased risk of becoming ill relative to an average member of the population and in need of such attention, care, or management. Treating can refer to prolonging survival as compared to expected survival if not receiving treatment. Thus, one of skill in the art realizes that a treatment may improve the disease condition, but may not be a complete cure for the disease. As used herein, the term "treatment" includes prophylaxis, and may further include the implementation of measures intended to reduce the subject's likelihood of contracting an infectious disease (e.g., COVID-19). For example, in certain aspects, the treatment may include medical and/or pharmacologic interventions intended to reduce the subject's likelihood of contracting an infectious disease (e.g., the prophylactic administration of one or more vaccines, convalescent plasma infusion and/or antibodies to the subject). In other embodiments, the treatment may include non-pharmacologic interventions, such as self-isolation and/or quarantine of a subject identified as being susceptible to developing an infectious disease and/or the associated complications. Alternatively, treatment is "effective" if the disease is prevented and/or if progression of a disease is reduced or halted. "Treatment" can also mean prolonging survival as compared to expected survival if not receiving treatment.

A treatment is not necessarily curative, and in certain aspects may reduce the effect of an infection by a certain percentage over an untreated infection. For example, treatment may reduce inflammation or reduce the presence of inflammatory cytokines in a subject suffering from an infection. In some embodiments, methods of treatment may be personalized medicine procedures, in which the DNA of an individual is analyzed to provide guidance on the appropriate therapy for that specific individual. The methods of the invention may provide guidance as to whether treatment is necessary or most effective, as well as revealing progress of the treatment and guiding the requirement for further treatment of the individual.

It should be noted that in certain aspects, the treatment may comprise the recommendation and/or implementation of measures intended to reduce the subject's likelihood of contracting an infection, and which measures are not isolated to the subject. For example, in certain embodiments, the treatment may comprise vaccinating members of the subject's community (e.g., family, co-workers and/or healthcare providers) in an effort to reduce the transmission of the infection.

In some embodiments, treatment comprises reducing the incidence of the presence of clonal hematopoiesis in the subject's blood. In other embodiments, treatment or monitoring includes repeating the sequencing of a blood sample of the subject monthly, bi-monthly, or quarterly, and reducing (or monitoring reduction in) the incidence of the presence of clonal hematopoiesis in the subject's blood. In some embodiments, treatment or monitoring comprises including the subject as a candidate to receive a bone marrow transplant. In some embodiments, treatment includes administering to the subject a bone marrow transplant. In some embodiments, treatment includes transfusing the subject with blood in which clonal hematopoiesis is absent.

In some aspects, a subject is identified as being high risk based on gene sequencing (e.g., performing a CHIP assessment). A subject identified as being high risk has an increased risk of contracting an infection and/or of having a serious reaction to an infection. In some aspects, high risk subjects are treated by early targeting of inflammation. For example, a high risk subject may be treated by administering pro-inflammatory driver inhibitors and/or low-dose hypomethylating drugs. In some embodiments, high risk subjects may be treated by vaccinating the subject and/or vaccinating members of the subject's community to reduce the transmission of the infection, and thereby reduce the likelihood that the subject will become infected.

In some aspects, vaccinating the subject and/or vaccinating members of the subject's community to reduce the transmission of the infection comprising the administration of a single vaccine dose or the administration of two vaccine doses. One or more vaccine boosters may optionally be administered after administration of the initial vaccine dose(s). For example, a vaccine booster may be administered about 6 months, 9 months, 12 months, 15 months, 18 months, 21 months, or 24 months after receiving the initial vaccine dose(s). In some aspects, a vaccine booster may be administered yearly. In some embodiments, the vaccine is an mRNA vaccine or a viral vector vaccine. In one embodiment, the vaccine is a BNT162b2 vaccine (a lipid nanoparticle-formulated,5 nucleoside-modified RNA (modRNA) encoding the SARS-CoV-2 full-length spike, modified by two proline mutations to lock it in the prefusion conformation). In one embodiment, the vaccine is a mRNA-1273 vaccine (a lipid nanoparticle-encapsulated mRNA-based vaccine that encodes the prefusion stabilized full-length spike protein of the severe acute respiratory syndrome coronavirus 2 (SARS-CoV-2)). In one embodiment, the vaccine is a Ad26.COV2.S Vaccine (a monovalent vaccine composed of a recombinant, replication-incompetent human adenovirus type 26 (Ad26) vector that encodes a SARS-CoV-2 spike (S) protein in a stabilized conformation). In one embodiment, the vaccine is a ChAdOx1 nCoV-19 vaccine (a replication-deficient chimpanzee adenoviral vector ChAdOx1, containing the SARS-CoV-2 structural surface glycoprotein antigen (spike protein; nCoV-19) gene).

In some aspects, treating a subject for an infection includes adjuvant treatment. For example, adjuvant treatment for preventing sequelae of acute pulmonary disease may include administration of one or more antiviral medications (e.g., remdesivir), anti-inflammatory medications, antibiotics, plasmapheresis, convalescent plasma infusion, monoclonal antibodies (e.g., bamlanivimab, etesevimab, casirivimab, imdevimab, recombinant humanized anti-interleukin-6 receptor monoclonal antibodies (e.g., tocilizumab)), corticosteroids (e.g., dexamethasone), supplemental oxygen, and mesenchymal stem cell/iPS cell therapy. In some aspects, adjuvant treatment for preventing sequelae of cardiac and/or infectious disease includes administration of one or more antiviral medications, anti-inflammatory medications, antibiotics, plasmapheresis, convalescent plasma, mesenchymal stem cell/iPS cell therapy, blood thinners, anti-arrhythmic drugs, and cardioprotective drugs. In certain aspects, blood pressure medications may be administered to a subject including angiotensin converting enzyme (ACE) inhibitors and/or angiotensin receptor blockers (ARBs).

In some embodiments, a subject's susceptibility to an infection is predicted using the sequencing and detection methods described herein. For example, a subject's susceptibility to an infection (e.g., a coronavirus infection) may be predicted by sequencing one or more nucleic acids selected from the group consisting of DNMT3A, TET2, ASXL1, PPM1D, JAK2, TP53, SRSF2, KRAS and SF3B1 from one or more cells in a blood sample of the subject; and detecting the presence of a mutation in the sequenced nucleic acids. In some embodiments, the presence of the mutation indicates an increased susceptibility to a coronavirus (e.g., COVID-19) infection. In some embodiments, a subject's increased mortality risk, e.g., resulting from a dysfunctional immune response, is predicted using the sequencing and detection methods described herein. In some aspects, the dysfunctional immune response is an inflammatory or interferon response.

In certain embodiments, a subject's susceptibility to an infection (e.g., a coronavirus infection) is predicted by sequencing DNMT3A and TET2 nucleic acids from one or more cells in a blood sample from the subject and detecting the presence of a mutation (e.g., mis-sense mutations or disruptive mutations) in the sequenced nucleic acids. The presence of a mutation in the sequenced DNMT3A and/or TET2 nucleic acids may indicate a subject's increased susceptibility to the infection.

In certain embodiments, the subject is a mammal, e.g., a primate, e.g., a human. The terms, "patient" and "subject" are used interchangeably herein. Preferably, the subject is a mammal. The mammal can be a human, non-human primate, mouse, rat, dog, cat, horse, or cow, but are not limited to these examples. In certain embodiments, the subject is a human.

The subject may be any age from birth to death, e.g., the subject may be an infant, a toddler, a child, a teenager, a young adult, or an adult. The subject may be at least about 1 day old, 1 year old, 5 years old, 10 years old, 20 years old, 30 years old, 40 years old, 50 years old, 60 years old, 70 years old, 80 years old, 90 years old, or 100 years old. In some embodiments, the subject is under the age of 40, between the ages of 40-60, or over the age of 60.

In other embodiments, the subject may exhibit one or more risk factors including asthma, chronic lung disease, interstitial lung disease, cystic fibrosis, pulmonary hypertension, chronic obstructive pulmonary disease (COPD), diabetes, obesity, being aged 65 years or older, heart condition (e.g., heart failure, coronary artery disease, cardiomyopathies, hypertension, etc.), high blood pressure, chronic kidney disease, immunocompromised (e.g., undergoing therapy for cancer), liver disease, dementia or other neurological condition, down syndrome, HIV infection, pregnancy, sickle cell disease or thalassemia, stroke or cerebrovascular disease, solid organ or blood stem cell transplant, substance use disorder, or history of being a smoker. In some embodiments, the subject has a comorbid condition selected from the group consisting of cardiovascular disease, lung disease, kidney disease, liver disease, neurological condition, cerebrovascular disease, diabetes, obesity, asthma, emphysema, and cancer.

It is to be understood that the invention is not limited in its application to the details set forth in the description or as exemplified. The invention encompasses other embodiments and is capable of being practiced or carried out in various ways. Also, it is to be understood that the phraseology and terminology employed herein is for the purpose of description and should not be regarded as limiting.

While certain compounds, compositions and methods of the present invention have been described with specificity in accordance with certain embodiments, the following examples serve only to illustrate the methods and compositions of the invention and are not intended to limit the same.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications and other reference materials referenced herein to describe the background of the invention and to provide additional detail regarding its practice are hereby incorporated by reference.

EXEMPLIFICATION

Example 1

A DNA microarray will be used to identify, and report inherited genetic variants (e.g., TET2, DNMT3A, ASXL1, PPM1D, JAK2, TP53, SRSF2, KRAS, and/or SF3B1) associated with a variety of cardiovascular and metabolic disorders, as well as with certain cancers. These cancers and disorders, if pre-existing, can increase the risk of death related to COVID 19 complications. Also included in this microarray are genetic variants associated with pro- and anti-inflammatory effects. Some of these include ACE2, CRP, IL-6R, IL-1A GC, and IL-10. Furthermore, the microarray may elucidate which inborn errors of immunity can cause life-threatening COVID 19 in previously healthy younger patients.

In addition, the microarray may test for various biomarkers present in the blood that are involved in immunity and inflammation, which may impact COVID 19 infection response. These biomarkers may include hsCRP, IL-6, IL-8, and TNF-alpha.

Clonal hematopoiesis of indeterminate potential (CHIP) is a genetic issue unique to nucleated cells contained within the blood. CHIP refers to the unhealthy expansion of the same set of detrimental mutations and damage to an individual's DNA in their nucleated blood cells. CHIP may potentially explain the age-related prevalence of inflammatory conditions. A connection between CHIP mutations and heart diseases is believed to be mediated by inflammation. It has been more recently postulated that CHIP may be associated with broader biological impact which may be explained by the fact that people with CHIP have an aberrant inflammatory system compared with those without CHIP. Specifically, recent research has demonstrated that structural DNA damage in genes such as TET2 and DNMT3A is associated with a dysfunctional response to inflammation and infection. In addition, key cytokines such as serum IL-6 and IL-8 have been shown to be elevated in people with CHIP, establishing its relevance to the human systemic inflammatory landscape and its impact on poorer health status, and increased and potentially novel comorbidities.

It is known that somatic exonic mutations are acquired at a rate of approximately 1.3 per hematopoietic stem cell per decade and are rarely detected in people under age 40 years. Clonal hematopoiesis increases with age and is found in approximately 10 percent of people without known hematologic malignancies older than 65 years, in almost 12 percent of those aged 80 to 89 years, and in more than 18 percent of those older than 90 years.

In addition to detecting and monitoring somatic changes associated with CHIP, a screen will also be performed for germline/inherited variants associated with cardiovascular disease, cancer, and inflammation. The association between CHIP, inflammation, and leukocyte dysfunction will be examined so the CHIP-related comorbidities in COVID 19 can be more effectively managed clinically. For example, the presence of CHIP as a disease modifier might explain why some patients are more responsive or refractory to treatments, or why some patients undergo more slow or rapid disease progression. Furthermore, this dynamic measurement may elucidate novel opportunities to develop new drug therapies focusing on the genetic abnormalities of CHIP.

Within the PBMCs that are isolated and preserved from the peripheral blood, a variety of potentially therapeutic cell types will be accessed, including small numbers of CD34+ hematopoietic stem cells (HSCs), T-cells and circulating endothelial progenitor cells (EPCs) that allow for the derivation of clinical grade induced pluripotent stem (iPS) cells. Notably iPS cells can be programmed to produce virtually any cell type in the human body, such as immune cells and alveolar cells of the lung which produce surfactant (AE2). AE2 cells play various roles in alveolar fluid balance, coagulation/fibrinolysis, and host defense. AE2 cells proliferate, differentiate into AE1 cells, and contribute to epithelial repair and immunoregulation. In addition, iPS cells can be differentiated into mesenchymal stem cells (MSCs) which are known to modulate the pro-inflammatory immune cytokine response which is largely responsible for the cascade of events leading to severe pulmonary disease. Whether these cells can restore healthy lung tissue after a COVID 19 infection will be examined. Blood-derived iPS cells represent a personalized cell resource for individuals to generate AE2 cells and cells of immune function as a therapy option.

We will provide genetic evaluation for a better understanding of the genetic history and at risk disease potential, tracking of biomarkers to evaluate progression of disease, measurement of somatic damage and mutations that may contribute to a deranged inflammatory response, and the opportunity to utilize stem cells in potential therapies, potentially including those for COVID 19 or other viral disease.

Example 2

CHIP is a genetic issue unique to the nucleated cells contained within blood. It refers to the unhealthy expansion of the same set of detrimental mutations and damage to an individual's DNA in their nucleated blood cells. CHIP may potentially explain the age-related prevalence of inflammatory conditions. A connection between CHIP mutations and heart diseases is believed to be mediated by inflammation. It has been more recently postulated that CHIP may be associated with broader biological impact which may be explained by the fact that people with CHIP have an aberrant inflammatory system compared with those without CHIP. Specifically, key cytokines such as serum IL-6 and IL-8 have been shown to be elevated in people with CHIP, establishing its relevance to the human systemic inflammatory landscape and its impact on poorer health status, and increased and potentially novel comorbidities.

It is known that somatic exonic mutations are acquired at a rate of approximately 1.3 per hematopoietic stem cell per decade, and are rarely detected in people under age 40 years. Clonal hematopoiesis increases with age and is found in approximately 10 percent of people without known hematologic malignancies older than 65 years, in almost 12 percent of those aged 80 to 89 years, and in more than 18 percent of those older than 90 years.

Whether an age-related increase in CHIP contributes to the age-related risk of COVID 19 will be assessed. If these phenomena are shown to be linked, the CHIP-related analysis will provide a quantifiable risk assessment. If the complex association between CHIP, inflammation, and leukocyte dysfunction can be unraveled, CHIP-related comorbidities in COVID 19 may be more effectively managed clinically. For example, the presence of CHIP as a disease modifier may explain why some patients are more responsive or refractory to treatments, or why some patients undergo more slow or rapid disease progression.

By monitoring acquired changes to both sequence and structure of the DNA within the blood it may ultimately provide an additional layer of insight into identifying those at increased risk for infection or COVID 19 complicated mortality. Somatic changes associated with CHIP may be detected and monitored, as well as screening for germline/inherited variants associated with cardiovascular disease, cancer, and inflammation. Blood samples will be evaluated with a target sequence panel specific to genes with somatic (accumulated) and germline (inherited) variants associated with CHIP, including but not limited to TET2 and DNMT3A, both of which have been associated with a dysfunctional response to inflammation and infection. In addition, microarray-based methods are used to measure somatic structural DNA variation and damage across the genome, additionally associated with CHIP. Genetic test results will be correlated with serologic and clinical data from the subject's medical record.

Example 3

Blood samples will be collected from a variety of subjects. The blood samples will be assessed to identify samples that are seropositive COVID 19, Influenza A, Influenza B, RSV, SARS-CoV, and MERS-CoV. In addition, normal control blood samples will also be obtained. The blood samples will be assayed for clonal hematopoiesis (CHIP) using an assay that screens for somatic variations in TET2, DNMT3A, ASXL1, PPM1D, JAK2, TP53, SRSF2, KRAS, and SF3B1.

Additional assessments will be performed on the blood samples including evaluating the samples for additional variants in other genes, as well as performing additional blood analysis. Further, clinical data will be collected for the subjects from who the blood samples were taken from.

In addition, the samples will be evaluated for one or more variants in ACE2, IFITM3, IL-1A, IL-1B, IL-6, IL-6R, CXCL8, IL-12A, IL-12B, IL-18, TNF-α, TNF-β, and TNF-γ. The samples will be assessed for additional features such as arterial blood gas, white count with differential (lymphocytes, neutrophils, cytokine levels, C-reactive protein (CRP), erythrocyte sedimentation rate (ESR), Lactase, MB-CK enzyme, etc.) Clinical data for the subjects from whom the blood samples are obtained will additionally be considered including, but not limited to, the development of any complications related to the diagnosis (MI, myocarditis, pulmonary embolism), vital signs, 02 sat, 02 requirements, intubation status, mortality, and cause(s) of death. Additionally, any imaging obtained from the subject will be considered, including chest X rays (CXR) and CT scans. Finally, any co-morbidities and family history will also be taken into consideration.

CHIP may be utilized as a disease modifier to explain why some COVID 19 patients undergo a faster and more severe disease progression, and why some patients are more responsive/refractory to treatments. In addition, CHIP may be utilized as a disease modifier in determining which patients are more susceptible to poor cardiac outcomes. CHIP may also be utilized to provide guidance on mitigation strategies for population management, e.g., establishing quarantine protocols and identifying groups of individuals to be quarantined, possibly more restrictively than other individuals.

Example 4

Introduction

The arrival of the newly discovered coronavirus in 2019 has impacted the world gravely, with over 136 million reported cases and over 3 million deaths worldwide. To date, no effective intervention strategies are in place, yet the emergence of mutant strains is dispersing rapidly. In addition, molecular rRT-PCR tests may result in false-negative or false-positive outcomes thereby questioning its status as 'golden standard' for laboratory diagnosis of coronavirus disease 2019 (COVID-19) (1). Novel effective diagnostic solutions could be the key to curbing the spread of COVID-19, as early diagnosis is crucial for controlling infectious propagation.

Severe Acute Respiratory Syndrome Coronavirus-2 (SARS-COV-2) is an enveloped single-stranded, positive-sense ribonucleic acid (ssRNA+) coronavirus which belongs to the family of Coronaviridae (2). The infection manifests itself as mild-moderate symptoms, such as coughing, muscle fatigue and fever to severe respiratory failure which requires ICU care and ventilation (3).

Important predictors of severe clinical outcomes are advanced age, gender and comorbid conditions including obesity, diabetes, cardiovascular diseases (CVDs) and chronic obstructive pulmonary disease (COPD) (4-7). Furthermore, emerging data indicate that uncontrolled inflammation is associated with disease severity. Indeed, unfettered release of pro-inflammatory cytokines such as IL-6, IL-2, IL-7 and TNF-alpha can cause a so-called cytokine storm, a potential life-threatening phenomenon frequently seen in COVID-19 patients with severe infection (8). In these patients, the hyperactive immune activation may progress to acute respiratory stress syndrome (ARDS) and multiple organ dysfunctions (9). The presence of a cytokine storm may contribute to cardiovascular complications, including unstable plaque formation, coronary artery occlusion, myocardial infarction and, eventually, transition to heart failure (10, 11).

While it is evident that inflammation and pre-existing comorbidities play a significant role in the pathogenesis of COVID-19, the presence of somatic acquired mutations has now been recognized as possibly another independent determinant for disease outcome (12, 26). These mutations are found in genes involved in epigenetic regulation including DNMT3A, TET2, ASXL1 and JAK2, and result in expansion of genetically identical clones of nucleated peripheral blood stem and progenitor cells. This phenomenon is referred to as clonal hematopoiesis of indeterminate potential (CHIP) and affects a large proportion (>10%) of the older population over the age of 70 (13). Individuals with CHIP are at an increased risk for developing CVDs, including aortic valve stenosis, venous thrombosis, and heart failure (14-16). Growing evidence indicates that the heightened risk might be due to hyper-inflammatory potential in these individuals (17-19). Indeed, a TET2 deletion has been associated with inflammasome activation and subsequent excessive levels of pro-inflammatory cytokines IL-6 and IL-1, whereas DNMT3A mutations have shown increased numbers of chemokines and reduced type-1-interferon secretion compared to non-CHIP carriers (20-23). Remarkably, however, individuals with large DNMT3A or TET2 CHIP-driver mutations (allele fraction of >10%) were protected from cardiovascular events if they also had a simultaneous germline sequence variation in the IL-6 receptor (IL-6R) (24). While most of these outcomes were studied in monocytes and macrophages, CHIP mutations have also been shown to alter the function of other leukocyte populations (25). Thus, the presence of CHIP might dysregulate the entire inflammatory system and therefore may corrupt disease outcome in COVID-19 patients.

In support of this notion, recent clinical data showed higher CHIP frequencies in patients with severe COVID-19 compared to the control population (26-27). It should be noted, however, that the control group of one study, referenced herein as the Duployez study (26) consisted mostly of individuals with unexplained cytopenia, thereby potentially introducing biases that underestimate the overall risk of CHIP. Furthermore, Shivarov, et al. consolidated data of four large studies on the frequency of CHIP and observed a linear correlation between the presence of CHIP clones and mortality rate in COVID-19-infected patients (12). This suggests that detection of CHIP may be predictive of fatal outcome in patients with COVID-19. However, to date no clinical studies have been identified that have conducted a comparison of CHIP prevalence to mild and severe COVID-19 symptoms.

In the present study, the hypothesis that CHIP is associated with disease severity in COVID-19 patients was tested. Three age groups were evaluated—under 40 years-old, 40-60 years old and those older than 65 years. While CHIP has been reported to be rare in younger people with frequencies of about 1 in 1000 in those younger than 40 and about 0.7% in those under 50, CHIP has been more recently found in higher frequencies in younger individuals with early-onset myocardial infarction and in some advanced autoimmune disease, and hence it was hypothesized that it could be a risk factor in younger populations with severe COVID-19 disease (27, 29).

Methods

Patients and Samples—Patient samples were collected both through collaboration and under the IRB of the New York Blood Center (NYBC) as well as via a prospective procurement contract through iSpecimen. Patients included in the study were confirmed to be PCR positive for SARS-CoV-2 infection and classified as either severe hospitalization or non-hospitalized. Severe hospitalized patients were defined as infected and admitted to the hospital for a minimum of seven days, with a priority towards patients admitted to the ICU and requiring oxygen support. Non-hospitalized patients were defined as infected and symptomatic (fever, loss of smell, body aches, coughing) or asymptomatic, but not requiring hospitalization. Samples were excluded from collection and/or analysis if the patient had previously received blood stem cell transplant or had undergone chemotherapy. Samples procured through NYBC were delivered as cryopreserved PBMCs while samples received from iSpecimen were supplied as frozen whole blood (WB).

Molecular Analysis—Genomic DNA (gDNA) was extracted from cryopreserved PBMC and frozen WB samples using the PerkinElmer Chemagic 360 B5K automated extraction platform. For targeted sequencing extracted gDNA was normalized and aliquoted to 25 ng/ul in 25 ul total volume. Custom DNA target sequencing libraries were constructed using Agilent SureSelect chemistry. The resulting libraries were analyzed on the Agilent 4200 TapeStation System and quantified by KAPA qPCR. Samples were sequenced using the Illumina MiSeq platform with an averages sequencing coverage >1000x across amplicons. DNA sequence quality was verified and then BAM (Binary Alignment/Map) and VCF (Variant Call Format) files were generated. Putative somatic variants were annotated against GenBank gene models and the ClinVar database. Both somatic and germline coding variants from genes DNMT3A, TET2, ASXL1, PPM1D, JAK2, TP53, SF3B1, SRSF2, and KRAS were extracted from the annotated VCF. Upon analysis CHIP accumulated/somatic variants were defined as having >1.5% variant allele frequency (VAF) and 20 or more variant cells.

For microarray analysis, extracted gDNA was normalized and aliquoted to 25 ng/ul in 50 ul total volume. Normalized and aliquoted gDNA samples were run on the Illumina Infinium™ Global Screening Array (GSA)—24 v2.0 BeadChip in the labs of Diagnomics (San Diego, Calif. USA). The resulting iDAT files were converted to GTC files using the Illumina Array Analysis Platform and a VCF file with genotype information was generated. SNP and indel markers were annotated against GenBank gene models and a table with all the genotyped markers from genes IL6R, CXCL8, IL6, and ACE2 were extracted from the VCF using the BCFtools+split-vep plugin.

Results

The study described herein assessed whether CHIP is associated with disease severity in COVID-19 patients by looking at three age groups of patients—under 40 years-old, 40-60 years old and older than 65 years. The most common somatic mutations identified were DNMT3A and TET2 in all groups, with 54% in those <60, and 71% in those over the age of 65. A summary of the individual groups is provided below.

Age Group Under 40

The cohort of severe disease in the under 40 group included 9 patients. Two patients (22.2%) had CHIP with VAF>1.5%. One of these patients had two CHIP mutations (DNMT3A and SF3B1) both with a VAF>1.5%. A third patient had a somatic mutation in TP53 with a VAF of 0.8% overall resulting in 3 patients (33.3%) having detectable somatic CHIP mutations. The expected frequency of CHIP in individuals under the age of 40 is about 0.1%. In addition, a fourth patient in this group had a germline mutation in TP53. Collection of samples from COVID-19 infected but non-hospitalized individuals in this age group is under way.

Age Group 40-60

The cohort in the 40-60 age group included 36 patients with severe disease and 4 non-hospitalized infected patients. Three (8.3%) of the 36 patients with severe disease had CHIP with VAF>1.5% with the following mutations: TET2, DNMT3A and KRAS. In addition, 7 additional patients with severe disease had CHIP mutations (3 with DNMT3A, 1 with TET2, 1 with KRAS and 1 with TP53) with a VAF<1.5%, overall resulting in 10 patients (27.8%) having detectable somatic CHIP mutations. The expected frequency of CHIP in a matched healthy 40-60 group would be approximately 2-3%. In addition, 5 patients had germline mutations in CHIP genes (3 with TET2, 1 with PP1MD, 1 with TP53). None of the 4 samples collected in non-hospitalized COVID19 infected patients in this age group demonstrated CHIP with a VAF>1.5%.

Age Group >65

This cohort includes 43 hospitalized patients with severe disease, 46 non-hospitalized infected patients and a historic control of 106 individuals. The median age for each group is 69.5, 68.7, and 82 respectively. The frequency of CHIP>1.5% VAF was 14%, 16%, 35% respectively.

TABLE 1

NYBC Study

| | >65 CHIP >1.5% | 40-60 CHIP >1.5% | <40 CHIP >1.5% |
|---|---|---|---|
| Severe | 6/43 (14%) | 3/36 (8.3%) | 2/9 (22%) |
| Mild | 7/45 (16%) | 0/4 (0%) | N/A |
| Healthy Population | (33%) | (2-3%) | (0.1%) |

Germline Mutations (IL-6R p. Asp358Ala Coding Mutation)

In addition, multiple studies have demonstrated the increased risk of cardiovascular disease in the presence of CHIP (17, 27). However, the risk of incident cardiovascular events such as myocardial infarction, stroke and death is abrogated in those with a simultaneous genetic deficiency of IL-6 signaling (IL-6R p Asp358Ala) (24). It is hypothesized that the increased risk of CVD is mediated by IL-6 signaling. Likewise, the severity of COVID-19 has been associated with a dysfunctional inflammatory response mediated by cytokines, particularly IL-6. In one example, a COVID-19 infected patient with two large clone CHIP mutations (JAK2 mutation with 76% VAF and TET2 mutation with 23% VAF) also had an IL-6R coding mutation which may have protected this patient from developing severe disease. In this study, 5.1% of patients with CHIP and a simultaneous genetic deficiency in IL-6 signaling (by carrying IL6R p.Asp358A1a) were non-hospitalized when infected with COVID-19. On the other hand, only 1.6% of patients with CHIP and this coding mutation developed severe COVID-19 disease. Therefore, genetically reduced IL-6 signaling may abrogate the risk of developing severe disease among carriers of CHIP.

Third Party Studies

Additional studies looking at the association of CHIP with COVID-19 have been conducted by other research groups. A first study is identified herein as the French study and described in Duployez, et al., (26), and a second study is identified herein as the MSK study and described in Bolton et al., (28). Both studies assessed the relationship between clonal hematopoiesis and the severity of a COVID-19 infection. The two studies are summarized below.

French Study (Duployez, 26):

122 patients hospitalized for COVID19. 76% male. 73% ICU.

A high prevalence of Clonal Hematopoiesis (25%, 38%, 56%, and 82% of patients aged <60 years, 60-70 years, 70-80 years, and >80 years) was reported compared to a retrospective cohort of patients explored within the same pipelines (10%, 21%, 37%, and 44%). 80% of those with CHIP had DNMT3A and/or TET2 mutations. After adjustment for age, the prevalence OR of CH was 3.182 (95% CI: 1.944-5.209, p<0.001) in COVID-19 patients.

TABLE 2

French Study summary

| Age | CHIP Positive | Control Group |
|---|---|---|
| <60 | 25% | 10% |
| 60-70 | 38% | 21% |

TABLE 2-continued

French Study summary

| Age | CHIP Positive | Control Group |
|---|---|---|
| 70-80 | 56% | 37% |
| >80 | 82% | 44% |

MSK STUDY (Bolton, 28):

Among 515 individuals with Covid-19 from Memorial Sloan Kettering (MSK) and the Korean Clonal Hematopoiesis (KoCH) consortia, it was found that CH was associated with severe Covid-19 outcomes (OR=1.9, 95%=1.2-2.9, p=0.01).

The first cohort was composed of patients with solid tumors treated at Memorial Sloan Kettering Cancer Center (MSK) with blood previously sequenced using MSK-IM-PACT, a previously validated targeted gene panel capturing all commonly mutated CH-associated genes. In the MSK cohort, CH was observed in 51% and 30% of patients with severe versus non-severe Covid-19, respectively (adjusted OR: 1.85, 95% CI 1.10-3.12).

The second cohort included 112 previously healthy individuals without cancer who were hospitalized for Covid-19 between January and April 2020 at four tertiary hospitals in South Korea (KoCH cohort). The KoCH cohort was sequenced using a custom targeted NGS panel from Agilent (89 genes) which was designed to include commonly occurring CH genes.

In the KoCH cohort, CH was observed in 25% and 15.9% of patients with severe versus non-severe Covid-19, respectively (adjusted OR 1.85, 95% CI 0.53-6.43). A comparative analysis of age groups was not performed.

TABLE 3

MSK Study summary

|  | Severe Chip− | Severe CHIP+ | Non-Severe Chip− | Control Non-Severe Chip+ | Odds Ratio |
|---|---|---|---|---|---|
| MSK | 46 | 48 | 223 | 96 | 1.85 |
| KoCH | 51 | 17 | 37 | 7 | 1.85 |

Discussion

The frequency of clonal hematopoiesis is rare in healthy individuals under 40 and uncommon in those under 60. The results from the study described herein demonstrate there is a relatively high frequency of CHIP in younger patients infected with COVID-19 who have been hospitalized with severe disease. And when lower VAFs were included in the analysis, this frequency increased further. CHIP may provide an explanation why some younger patients infected with COVID-19 have a clinical course that requires hospitalization. This is consistent with prior studies implicating CHIP in dysfunctional inflammatory responses with elevated cytokines and decreased interferons which is the typical profile of patients with severe disease (REF). Therefore, this would be the presumed mechanism in the younger cohort with severe disease in our study. Furthermore, acute and chronic cardiovascular events are a frequent cause of morbidity and mortality in hospitalized COVID-19 patients and CHIP has been highly associated with cardiovascular diseases such as myocardial infarction and stroke. Not only is CHIP a significant risk factor for myocardial infarction of all ages, but the risk is highest in younger patients who demonstrates early-onset myocardial infarction (27). Mutations in DNMT3A and TET2 were each individually associated with coronary heart disease and in fact, these were the most frequently mutated in the CHIP patients with severe disease who were assessed in the study described herein.

The data to date does not show a higher frequency of CHIP in individuals >65 years old with severe disease compared to the control groups as was demonstrated in two recent studies (26, 28). It was hypothesized that the presence of other comorbidities in the older patients in the study contribute to a similar degree as CHIP and these comorbidities are less frequent in younger populations.

Regarding the younger cohort, while there is a paucity of literature studying younger individuals with CHIP, a few recent studies have identified younger patients with severe autoimmune diseases as having CHIP. For example, CHIP was found with a relatively high frequency in patients with RA, but particularly in those with clinically advanced and refractory disease and including some patients in their 30s (BMJ).

The data provided from this study also demonstrates that genetically reduced IL-6 signaling which has been previously shown to be protective for cardiovascular insults may abrogate the risk of developing severe disease among carriers of CHIP.

REFERENCES

1. Tahamtan, A., and A. Ardebili. 2020. Real-time RT-PCR in COVID-19 detection:
issues affecting the results. *Expert Rev Mol Diagn* 20: 1-2.
2. Lotfi, M., M. R. Hamblin, and N. Rezaei. 2020. COVID-19: Transmission, prevention, and potential therapeutic opportunities. *Clin Chim Acta* 508: 254-266.
3. Grant, M. C., L. Geoghegan, M. Arbyn, Z. Mohammed, L. McGuinness, E. L. Clarke, and R. G. Wade. 2020. The prevalence of symptoms in 24,410 adults infected by the novel coronavirus (SARS-CoV-2; COVID-19): A systematic review and meta-analysis of 148 studies from 9 countries. *Plos One* 15: e0234765.
4. Lauc, G., and D. Sinclair. 2020. Biomarkers of biological age as predictors of COVID-19 disease severity. *Aging Albany Ny* 12: 6490-6491.
5. Xiao, W.-W., J. Xu, L. Shi, Y.-D. Wang, and H.-Y. Yang. 2020. Is chronic obstructive pulmonary disease an independent predictor for adverse outcomes in coronavirus disease 2019 patients? *Eur Rev Med Pharmaco* 24: 11421-11427.
6. Ou, M., J. Zhu, P. Ji, H. Li, Z. Zhong, B. Li, J. Pang, J. Zhang, and X. Zheng. 2020. Risk factors of severe cases with COVID-19: a meta-analysis. *Epidemiol Infect* 148: e175.
7. Zhang, J., X. Dong, Y. Cao, Y. Yuan, Y. Yang, Y. Yan, C. A. Akdis, and Y. Gao. 2020. Clinical characteristics of 140 patients infected with SARS-CoV-2 in Wuhan, China. *Allergy* 75: 1730-1741.
8. Huang, C., Y. Wang, X. Li, L. Ren, J. Zhao, Y. Hu, L. Zhang, G. Fan, J. Xu, X. Gu, Z. Cheng, T. Yu, J. Xia, Y. Wei, W. Wu, X. Xie, W. Yin, H. Li, M. Liu, Y. Xiao, H. Gao, L. Guo, J. Xie, G. Wang, R. Jiang, Z. Gao, Q. Jin, J. Wang, and B. Cao. 2020. Clinical features of patients infected with 2019 novel coronavirus in Wuhan, China. *Lancet* 395: 497-506.
9. Zhou, F., T. Yu, R. Du, G. Fan, Y. Liu, Z. Liu, J. Xiang, Y. Wang, B. Song, X. Gu, L. Guan, Y. Wei, H. Li, X. Wu, J. Xu, S. Tu, Y. Zhang, H. Chen, and B. Cao. 2020. Clinical course and risk factors for mortality of adult inpatients with COVID-19 in Wuhan, China: a retrospective cohort study. *Lancet* 395: 1054-1062.

10. Unudurthi, S. D., P. Luthra, R. J. C. Bose, J. McCarthy, and M. I. Kontaridis. 2020. Cardiac inflammation in COVID-19: Lessons from heart failure. *Life Sci* 260: 118482.
11. Magadum, A., and R. Kishore. 2020. Cardiovascular Manifestations of COVID-19 Infection. *Cells* 9: 2508.
12. Shivarov, V., and M. Ivanova. 2020. Clonal haematopoiesis and COVID-19: A possible deadly liaison. *Int J Immunogenet* 47: 329-331.
13. Jaiswal, S., P. Fontanillas, J. Flannick, A. Manning, P. V. Grauman, B. G. Mar, R. C. Lindsley, C. H. Mermel, N. Burtt, A. Chavez, J. M. Higgins, V. Moltchanov, F. C. Kuo, M. J. Kluk, B. Henderson, L. Kinnunen, H. A. Koistinen, C. Ladenvall, G. Getz, A. Correa, B. F. Banahan, S. Gabriel, S. Kathiresan, H. M. Stringham, M. I. McCarthy, M. Boehnke, J. Tuomilehto, C. Haiman, L. Groop, G. Atzmon, J. G. Wilson, D. Neuberg, D. Altshuler, and B. L. Ebert. 2014. Age-Related Clonal Hematopoiesis Associated with Adverse Outcomes. *New Engl J Medicine* 371: 2488-2498.
14. Mas-Peiro, S., J. Hoffmann, S. Fichtlscherer, L. Dorsheimer, M. A. Rieger, S. Dimmeler, M. Vasa-Nicotera, and A. M. Zeiher. 2019. Clonal haematopoiesis in patients with degenerative aortic valve stenosis undergoing transcatheter aortic valve implantation. *Eur Heart J* 41: 933-939.
15. Sano, S., Y. Wang, Y. Yura, M. Sano, K. Oshima, Y. Yang, Y. Katanasaka, K.-D. Min, S. Matsuura, K. Ravid, G. Mohi, and K. Walsh. 2019. JAK2 V617F-Mediated Clonal Hematopoiesis Accelerates Pathological Remodeling in Murine Heart Failure. *Jacc Basic Transl Sci* 4: 684-697.
16. Bazeley, P., R. Morales, and W. H. W. Tang. 2020. Evidence of Clonal Hematopoiesis and Risk of Heart Failure. *Curr Hear Fail Reports* 17: 271-276.
17. Jaiswal, S., and P. Libby. 2020. Clonal haematopoiesis: connecting ageing and inflammation in cardiovascular disease. *Nat Rev Cardiol* 17: 137-144.
18. Yura, Y., S. Sano, and K. Walsh. 2020. Clonal Hematopoiesis: A New Step Linking Inflammation to Heart Failure. *Jacc Basic Transl Sci* 5: 196-207.
19. Abplanalp, W. T., S. Cremer, D. John, J. Hoffmann, B. Schuhmacher, M. Merten, M. A. Rieger, M. Vasa-Nicotera, A. M. Zeiher, and S. Dimmeler. 2021. Clonal Hematopoiesis—Driver DNMT3A Mutations Alter Immune Cells in Heart Failure. *Circ Res* 128: 216-228.
20. Fuster, J. J., S. MacLauchlan, M. A. Zuriaga, M. N. Polackal, A. C. Ostriker, R. Chakraborty, C.-L. Wu, S. Sano, S. Muralidharan, C. Rius, J. Vuong, S. Jacob, V. Muralidhar, A. A. B. Robertson, M. A. Cooper, V. Andres, K. K. Hirschi, K. A. Martin, and K. Walsh. 2017. Clonal hematopoiesis associated with TET2 deficiency accelerates atherosclerosis development in mice. *Science* 355: 842-847.
21. Sano, S., K. Oshima, Y. Wang, S. MacLauchlan, Y. Katanasaka, M. Sano, M. A. Zuriaga, M. Yoshiyama, D. Goukassian, M. A. Cooper, J. J. Fuster, and K. Walsh. 2018. Tet2-Mediated Clonal Hematopoiesis Accelerates Heart Failure Through a Mechanism Involving the IL-1β/NLRP3 Inflammasome. *J Am Coll Cardiol* 71: 875-886.
22. Wang, Y., S. Sano, Y. Yura, Z. Ke, M. Sano, K. Oshima, H. Ogawa, K. Horitani, K.-D. Min, E. Miura-Yura, A. Kour, M. A. Evans, M. A. Zuriaga, K. K. Hirschi, J. J. Fuster, E. M. Pietras, and K. Walsh. 2020. Tet2-mediated clonal hematopoiesis in non-conditioned mice accelerates age-associated cardiac dysfunction. *Jci Insight* 2020 Mar. 26; 5(6).
23. Rauch, P. J., A. J. Silver, J. Gopakumar, M. McConkey, E. Sinha, M. Fefer, E. Shvartz, G. Sukhova, P. Libby, B. L. Ebert, and S. Jaiswal. 2018. Loss-of-Function Mutations in Dnmt3a and Tet2 Lead to Accelerated Atherosclerosis and Convergent Macrophage Phenotypes in Mice. *Blood* 132: 745-745.
24. Bick, A. G., J. P. Pirruccello, G. K. Griffin, N. Gupta, S. Gabriel, D. Saleheen, P. Libby, S. Kathiresan, and P. Natarajan. 2019. Genetic IL-6 Signaling Deficiency Attenuates Cardiovascular Risk in Clonal Hematopoiesis. *Circulation* 141: 124-131.
25. Cook, E. K., M. Luo, and M. J. Rauh. 2020. Clonal hematopoiesis and inflammation: partners in leukemogenesis and comorbidity. *Exp Hematol* 83: 85-94.
26. Duployez, N., J. Demonchy, C. Berthon, J. Goutay, M. Caplan, A.-S. Moreau, A. Bignon, A. Marceau-Renaut, D. Garrigue, I. Raczkiewicz, S. Geffroy, M. Bucci, K. Alidjinou, J. Demaret, M. Labalette, T. Brousseau, A. Dupont, A. Rauch, J. Poissy, S. Susen, C. Preudhomme, and B. Quesnel. 2020. Clinico-Biological Features and Clonal Hematopoiesis in Patients with Severe COVID-19. *Cancers* (2020) 12(7): 1992.
27. S. Jaiswal, P. Natarajan, A. J. Silver, C. J. Gibson, A. G. Bick, E. Shvartz, M. McConkey, N. Gupta, S. Gabriel, D. Ardissino, U. Baber, R. Mehran, V. Fuster, J. Danesh, P. Frossard, D. Saleheen, O. Melander, G. K. Sukhova, D. Neuberg, P. Libby, S. Kathiresan, and B. L. Ebert. Clonal Hematopoiesis and Risk of Atherosclerotic Cardiovascular Disease N Engl J Med 2017; 377:111-121.
28. Bolton, K., Youngil Koh, Michael B. Foote, Hogune Im, et al. Clonal hematopoiesis is associated with risk of severe Covid-19. medRxiv 2020. 11.25.20233163.
29. Savola, P., Lundgren, S., Keränen, M. A. I. et al. Clonal hematopoiesis in patients with rheumatoid arthritis. *Blood Cancer Journal* 8, 69 (2018).
30. Tariq F, Alobaidi B, Xavier M on behalf of Human Dendritic Cell Lab, Newcastle University, United Kingdom, et al HU0026 CLONAL HAEMATOPOIESIS ASSOCIATED SOMATIC MUTATIONS IN RHEUMATOID ARTHRITIS *Annals of the Rheumatic Diseases* 2020; 79:226.
31. Tyrrell, D. J., Goldstein, D. R. Ageing and atherosclerosis: vascular intrinsic and extrinsic factors and potential role of IL-6. *Nat Rev Cardiol* 18, 58-68 (2021).
32. Pedersen K M, Çolak Y, Ellervik C, et al. Loss-of-function polymorphism in IL6R reduces risk of JAK2V617F somatic mutation and myeloproliferative neoplasm: A Mendelian randomization study. Eclinicalmedicine. 2020 April; 21:100280.

What is claimed is:

1. A method of treating a subject at risk of developing a severe complication from Coronavirus disease 2019 (COVID-19) infection, the method comprising
   determining whether the subject has clonal hematopoiesis of indeterminate potential (CHIP), wherein the step of determining whether the subject has CHIP comprises sequencing at least part of the genome of one or more cells in a blood sample of the subject to identify a mutation in one or more genes selected from the group consisting of DNMT3A, TET2, ASXL1, PPM1D, JAK2, TP53, SRSF2, KRAS and SF3B1, wherein the presence of said mutation indicates that the subject is at risk of developing a severe complication from COVID-19 infection; and
   treating the subject identified as being at risk of developing a severe complication from COVID-19, wherein treating the subject comprises administering to the subject a vaccine to reduce the subject's likelihood of contracting a severe complication from COVID-19 infection.

2. The method of claim 1, wherein the subject is under the age of 40.

3. The method of claim 1, wherein the one or more cells in the blood sample are nucleated cells.

4. The method of claim 1, wherein the one or more cells in the blood sample are somatic cells.

5. The method of claim 1, wherein the mutation is a somatic mutation in DNMT3A and/or TET2.

6. The method of claim 1, wherein the mutation is in DNMT3A in exons 7 to 23.

7. The method of claim 1, wherein the mutation is a mis-sense mutation in DNMT3A selected from the group consisting of G543C, S714C, F732C, Y735C, R736C, R749C, F751C, W753C, and L889C.

8. A method of treating a subject at risk of developing a severe coronavirus infection comprising determining whether the subject has clonal hematopoiesis of indeterminate potential (CHIP), wherein the step of determining whether the subject has CHIP comprises sequencing at least part of the genome of one or more cells in a blood sample of the subject to identify a mutation in one or more genes selected from the group consisting of DNMT3A, TET2, ASXL1, PPM1D, JAK2, TP53, SRSF2, KRAS and SF3B1; and wherein the presence of said mutation indicates that the subject has CHIP and is at risk of developing a severe coronavirus infection; and treating the subject having CHIP by administering a treatment selected from the group consisting of a vaccine, an antiviral medication, monoclonal antibodies, and combinations thereof, to reduce the subject's risk of developing a severe coronavirus infection.

9. The method of claim 8, wherein the coronavirus is selected from the group consisting of severe acute respiratory syndrome coronavirus (SARS-CoV), Middle East respiratory syndrome coronavirus (MERS-CoV), and severe acute respiratory syndrome coronavirus 2 (SARS-CoV-2).

10. The method of claim 8, wherein the coronavirus comprises severe acute respiratory syndrome coronavirus 2 (SARS-CoV-2) or COVID-19.

11. The method of claim 10, wherein the treatment is a vaccine.

12. The method of claim 8, wherein the subject is under the age of 40.

13. The method of claim 8, wherein the one or more cells in the blood sample are nucleated cells.

14. The method of claim 8, wherein the one or more cells in the blood sample are somatic cells.

15. The method of claim 8, wherein the mutation is a somatic mutation in DNMT3A and/or TET2.

16. The method of claim 8, wherein the mutation is in DNMT3A in exons 7 to 23.

17. The method of claim 8, wherein the mutation is a mis-sense mutation in DNMT3A selected from the group consisting of G543C, S714C, F732C, Y735C, R736C, R749C, F751C, W753C, and L889C.

18. A method of treating a subject at risk of developing a severe COVID-19 infection comprising:
   a. sequencing DNMT3A nucleic acids from one or more cells in a blood sample of a subject;
   b. detecting the presence of a mis-sense mutation in the sequenced DNMT3A nucleic acids;
   c. sequencing TET2 nucleic acids from one or more cells in the blood sample of the subject;
   d. detecting the presence of a disruptive mutation in the sequenced TET2 nucleic acids, wherein the presence of a mis-sense mutation in the sequenced DNMT3A nucleic acids and/or the TET2 nucleic acids indicates the subject is at risk of developing a severe COVID-19 infection; and
   e. administering to the subject a treatment selected from the group consisting of a vaccine, an antiviral medication, monoclonal antibodies, and combinations thereof, to reduce the subject's risk of developing the severe COVID-19 infection.

19. The method of claim 18, wherein the treatment is a vaccine.

20. The method of claim 8, wherein the treatment is an antiviral medication.

\* \* \* \* \*